United States Patent [19]

Suzuki et al.

[11] 4,175,543

[45] Nov. 27, 1979

[54] VENIPUNCTURE METHOD

[75] Inventors: Fred K. Suzuki, Arlington Heights; Thomas W. Davison, Streamwood, both of Ill.

[73] Assignee: Liquid Crystal Products, Inc., Arlington Heights, Ill.

[21] Appl. No.: 889,284

[22] Filed: Mar. 23, 1978

Related U.S. Application Data

[63] Continuation-in-part of Ser. No. 716,376, Aug. 23, 1976, abandoned, which is a continuation-in-part of Ser. No. 658,407, Feb. 17, 1976, Pat. No. 4,015,591.

[51] Int. Cl.$^2$ .............................................. A61B 10/00
[52] U.S. Cl. .................................... 128/736; 128/760
[58] Field of Search ....................... 128/2 H, 2 R, 403

[56] References Cited

U.S. PATENT DOCUMENTS

| | | | |
|---|---|---|---|
| 2,237,971 | 4/1941 | Padelford | 128/403 |
| 3,998,210 | 12/1976 | Nosari | 128/2 H |

*Primary Examiner*—William E. Kamm
*Attorney, Agent, or Firm*—Gerlach & O'Brien

[57] ABSTRACT

A method of effecting venipuncture in the human body includes the steps of cooling the skin over a venous area of the body by applying a cold pack thereto and providing on the cooled skin in heat exchange relation thereto a layer of an enantiotropic cholesteric liquid crystalline phase material exhibiting a mesophase color change at a temperature reached by the skin due to venous blood flow, warming the cooled skin by venous blood flow in such area thereby to produce a mesophase color change in the material delineating a vein therebeneath, and directing an instrument for venipuncture to a site in such area indicated by the delineation to constitute the location of a vein.

20 Claims, 1 Drawing Figure

COOL SKIN OVER VENOUS AREA
OF THE BODY BY APPLYING A
COLD PACK FOR AT LEAST 3
SECONDS AND PROVIDE A LIQUID
CRYSTAL LAYER ON COOLED SKIN

WARM COOLED SKIN BY VENOUS
BLOOD FLOW THEREBY TO
PRODUCE A COLOR CHANGE IN
LAYER INDICATING SITE OF A VEIN

DIRECT VENIPUNCTURE INSTRUMENT
TO INDICATED VEIN SITE

COOL SKIN OVER VENOUS AREA
OF THE BODY BY APPLYING A
COLD PACK FOR AT LEAST 3
SECONDS AND PROVIDE A LIQUID
CRYSTAL LAYER ON COOLED SKIN
WARM COOLED SKIN BY VENOUS
BLOOD FLOW THEREBY TO
PRODUCE A COLOR CHANGE IN
LAYER INDICATING SITE OF A VEIN
DIRECT VENIPUNCTURE INSTRUMENT
TO INDICATED VEIN SITE

VENIPUNCTURE METHOD

RELATED APPLICATION

This application is a continuation-in-part of our co-pending application Ser. No. 716,376, filed Aug. 23, 1976, now abandoned, which in turn is a continuation-in-part of our application Ser. No. 658,407, filed Feb. 17, 1976, now U.S. Pat. No. 4,015,591.

BACKGROUND OF THE INVENTION

This invention relates to a method of effecting venipuncture in the human body, for such purposes as drawing blood and making intravenous injections and infusions. More particularly, the invention relates to a venipuncture method employing an enantiotropic cholesteric liquid crystalline phase material for vein location.

Conventional venipuncture methods as long practiced have suffered from disadvantages and shortcomings which affect the patient in varying degrees of seriousness. With increasing proportions of less-qualified technicians, who may be trained only in blood-drawing, difficulties encountered during venipuncture for out-patient and in-patient blood drawing, blood banking, and I.V. therapy have increased. The problems are minimized when the veins are readily visible and/or palpable. However, it happens frequently that the vein locations are not readily visible or palpable, and where the veins are palpable but not visible, it may be difficult to determine the best site for needle insertion. Lacking in visibility, and even after application of a tourniquet, it frequently happens that the technician misses the vein with a needle and must probe until the needle hits the vein, or multiple insertions of the needle are required, which are painful procedures. In certain procedures, such as in an intravenous pylogram, in which a radioopaque contrast media (X-ray dye) is injected into the vein, an improper injection can cause subcutaneous skin damage. Problems are encountered when patients require frequent blood drawing during long hospitalization or extensive testing, and repeated venipuncture at the same site causes bruising, edema, scarring, and/or hardening of the vein and surrounding tissues. The veins then become less visible and palpable, venous blood flow is reduced, and the needle does not penetrate the scarred or hardened tissue readily. Under such circumstances, and also when patients require repeated intravenous administration during long I.V. therapy or due to complications, new injection sites may be required and often are difficult to find.

There is, therefore, a need for a rapid method of greater reliability for locating veins in the human body, in hospitals, clinics and laboratories, preparatory to drawing blood or making intravenous injections or infusions. It would be advantageous to provide a venipuncture method which overcomes the prior difficulties by indicating the best vein site and direction for needle insertion and, even more advantageously, providing information about the depth of the vein and its blood blow.

Cholesteric liquid crystalline phase materials, also referred to as cholesteric liquid crytals, their technology and applications are reviewed in the book by Peter L. Carroll entitled "Cholesteric Liquid Crystals," June, 1973 (Ovum Ltd., London). The materials, hereinafter referred to at times for convenience simply as "liquid crystals," are a class of compounds that display a cholesteric mesophase within certain temperature limits. The cholesteric mesophase is a state of matter intermediate in molecular ordering between a crystalline solid and an isotropic liquid. In general, the materials are colorless in their solid and isotropic liquid states, assuming the coloration of their background or of light-absorptive materials added thereto. When liquid crystals are in the cholesteric mesophase, and ordinary white light is directed at the material, the light is separated essentially into two components, one of which is transmitted and one of which is scattered or reflected. The scattered light gives the material an iridescent color, which depends upon the material, the temperature, and the angle of the incident light beam.

Prior patents relating to thermal color-responsive or temperature-sensitive cholesteric liquid crystal compositions and their use in applications where temperature is to be measured or a temperature pattern is to be observed include U.S. Pat. Nos. 3,114,836, 3,441,513 and 3,533,399, the latter patent having to do with the production of visible patterns corresponding to skin temperature patterns in human beings. Reports on the application of liquid crystal thermography to examination of the body include an article by Davison, Ewing, Fergason, Chapman, Can, and Voorhis, "Detection of Breast Cancer by Liquid Crystal Thermography," Cancer, Vol. 29, No. 5, page 1123, May, 1972, and an article by Davison, Ewing, Sayat, Mulla, and Fergason, "Liquid Crystal Thermographic Placental Location," *Obstetrics and Gynecology*, Vol. 42, No. 4, page 574, October, 1973.

In order to improve color contrast, the liquid crystals commonly are applied to and viewed against an absorptive, particularly a black background, which serves to absorb the transmitted light. Alternatively, absorptive, generally black particulate material is admixed with the liquid crystals, so as to absorb the transmitted light while not interfering excessively with the intensity of the scattered light. As an additional alternative, it has been proposed to incorporate black or colored dyes in the liquid crystal compositions.

The most common technique for applying liquid crystals to measure or map temperatures, as on a surface of the body, is to first blacken the surface with an aqueous, oil-impervious black paint, then apply liquid crystals from a solution by brushing or spraying. Liquid crystals dispersed in films and having a black backing or black filler for absorbing transmitted light have been applied to surfaces, including body skin, for measuring temperatures and for thermal mapping. Encapsulated liquid crystals are employed in a laminated article including a black background for locating veins in the body, in a venipuncture method disclosed in U.S. Pat. No. 3,998,210.

SUMMARY OF THE INVENTION

The invention provides a method of effecting venipuncture in the human body which fills the need for a rapid and reliable technique, especially for locating the deeper and more difficult to locate subcutaneous veins. When veins are not readily visible or palpable, they can be located more quickly and precisely, the best vein is located, and the direction for needle insertion is determined. When patients require frequent blood drawing at the same site, so that venipuncture becomes difficult to perform, the vein may be located and evaluated, or an alternate vein may be located. Similarly, a vein may be evaluated or a new vein located when a patient requires repeated intravenous administration or complications arise during long term I.V. therapy. When veins are not prominent for intravenous injection or infusion catheterization, the method may be employed to select the best vein site and direction for catheter insertion. The vein with the greatest blood flow may be selected, which insures longer patency and minimizes the risk of phlebitus. In all cases, the new method minimizes patient discomfort and anxiety during venipuncture, as resticking and probing with the needle is minimized. More objective information for locating and evaluating veins for venipuncture is provided.

The method of effecting venipuncture according to the invention includes the steps of: (a) cooling the skin over a venous area of the body by applying a cold pack thereto for a period of at least 3 seconds and providing on the cooled skin in heat exchange relation thereto a layer of an enantiotropic cholesteric liquid crystalline phase material a mesophase color change at a temperature reached by the skin upon warming by venous blood flow, the lower limit of the mesophase temperature range of the material being below the initial temperature of the skin over said area, the cooling being effected to bring the skin over the area to a temperature below said lower limit; (b) warming the cooled skin by venous blood flow in said area thereby to produce a mesophase color change in the material in said layer delineating a vein beneath the layer; and (c) directing an instrument for venipuncture to a site in said area indicated by said delineation to constitute the location of a vein.

BRIEF DESCRIPTION OF THE DRAWING

The drawing is a flow chart describing in summary form the steps of the venipuncture method of the invention.

DESCRIPTION OF THE PREFERRED EMBODIMENTS

Enantiotropic cholesteric liquid crystalline phase materials or liquid crystals which may be employed in the invention are well-known and readily may be selected for intended uses following the teachings of the prior art, including the patents and publications cited above. Thus, for example, liquid crystals which may be employed are described in detail in U.S. Pat. Nos. 3,114,836, 3,441,513, and 3,533,399. Most commonly, two, three or four-component liquid crystal compositions are employed, for providing a desired color response, and a mesophase or color-play temperature range at a desired temperature level and having a suitable width of temperature range. Preferably, the liquid crystals are selected to provide a color response in the mesophase range changing with increasing temperature from red through orange, yellow, green, and blue to violet in the visible spectrum, as a result of light scattering by the liquid crystals. Reference to an "enantiotropic" material means a liquid crystal which forms, or a mixture of liquid crystals which together form the cholesteric mesophase either by heating the material in its crystalline solid phase or by cooling the material in its isotropic liquid phase.

Preferred liquid crystals include the cholesteryl, dicholesteryl, cholestanyl, and sitosteryl organic esters, halides and alkyl carbonates. Table 1 is a list of liquid crystals which are further preferred in the invention.

Table 1

| | |
|---|---|
| Cholesteryl erucyl carbonate | (CEC) |
| Cholesteryl methyl carbonate | (GMC) |
| Cholesteryl oleyl carbonate | (COC) |
| CHolesteryl para-nonyl phenyl carbonate | (CNPC) |
| Cholesteryl phenyl carbonate | (CPC) |
| Cholesteryl acetate | (CA) |
| CHolesteryl benzoate | (CBz) |
| Cholesteryl butyrate | (CB) |
| Cholesteryl isobutyrate | (CiB) |
| Cholesteryl chloride | (CCl) |
| Cholesteryl chloroacetate | (CCA) |
| Cholesteryl cinnamate | (CCn) |
| Cholesteryl crotanoate | (CCr) |
| Cholesteryl decanoate | (CDc) |
| Cholesteryl erucate | (CE) |
| Cholesteryl heptanoate | (CHp) |
| Cholesteryl hexanoate | (CHx) |
| Cholesteryl myristate | (CMy) |
| Cholesteryl nonanoate | (CN) |
| Cholesteryl octanoate | (COt) |
| Cholesteryl oleate | (CO) |
| Cholesteryl propionate | (CP) |
| Cholesteryl valerate | (CV) |
| Dichloresteryl carbonate | (DCC) |
| Cholestanyl Benzoate | (CaBz) |
| Sitosteryl nonanoate | (SN) |

Preferred liquid crystal compositions and their mesophase temperature ranges are listed in Table 2.

Table 2

| Comp. No. | Components of Composition in % by weight | | | | Mesophase Temperature Range, °C. |
|---|---|---|---|---|---|
| 1. | 52% CN | 32% COC | 7% CBz | 9% DCC | 31–34 |
| 2. | 60% CN | 25% COC | 15% CBz | | 30–37 |
| 3. | 56% CN | 35% COC | 9% CBz | | 32–35 |
| 4. | 75% CN | 9% COC | 16% CP | | 29–37 |
| 5. | 75% CN | 10% COC | 15% CA | | 30–38 |
| 6. | 78% CN | 5% COC | 17% CP | | 34–37 |
| 7. | 85% CN | 5% COC | 10% CV | | 30–36 |
| 8. | 50% CN | 26% COC | 14% CBz | 10% CNPC | 29–33 |
| 9. | 50% CN | 33% COC | 8% CBz | 9% DCC | 28–33 |
| 10. | 56% CN | 44% COC | | | 31–32 |
| 11. | 48% CN | 44% COC | 8% DCC | | 31–33 |
| 12. | 47% CN | 43% COC | 7% DCC | 3% CCl | 30–33 |
| 13. | 23% CN | 60% CO | 17% CCr | | 29–31 |
| 14. | 70% CEC | 15% CCr | 15% CPC | | 28–30 |
| 15. | 40% CN | 40% CO | 5% CCr | 15% CaBz | 30–34 |
| 16. | 5% CN | 80% CO | 6% CCr | 15% CaBz | 33–36 |
| 17. | 51% CN | 35% COC | 8% CBz | 6% DCC | 30–33 |
| 18. | 48% CN | 40% COC | 4% CMC | 8% DCC | 29–32 |
| 19. | 64% CN | 27% COC | 2% CBz | 7% CMC | 27–33 |
| 20. | 57% CN | 38% COC | 5% CMC | | 29–32 |
| 21. | 59% CN | 35% COC | 3% CBz | 3% CA | 30–33 |

Table 2-continued

| Comp. No. | Components of Composition in % by weight | | | | Mesophase Temperature Range, °C. |
|---|---|---|---|---|---|
| 22. | 38% CN | 51% COC | 5% CBz | 6% DCC | 27–30 |
| 23. | 37% CN | 50% COC | 7% CBz | 6% DCC | 25–28 |

Body skin temperatures in general may range from about 28° C. to 37° C. in venous areas, and may go down to 21° C. or up to 39° C. The skin temperature varies over the surface of the body. For example, it may vary 6° C. around the circumference of the arm at the elbow, with the atmosphere at room temperature. It is preferred that compositions for application to the body have a mesophase temperature range in the range of about 20°–40° C., more preferably, 23°–33° C. The width of the mesophase temperature range preferably is from about 1° C. to about 7° C. in venipuncture applications. Greater color differentiation is obtained between areas of differing temperatures as the width of the temperature range increases, and temperature sensitivity increases with decreasing width of the range.

The liquid crystal composition for venipuncture use is selected to exhibit a mesophase color change at a temperature reached by the skin upon warming due to venous blood flow. Preferably, the initial or normal skin temperature above the vein falls within or above the mesophase temperature range. It is further preferred that the initial skin temperature above the vein be at least about as high as the upper limit of the mesophase temperature range, or, as otherwise stated, that the upper limit of such range be at most about equal to the initial skin temperature.

The maximum skin temperatures observed in the antecubital fossa and upper forearm regions of the arm, the most frequent sites for venipuncture, i.e., the temperatures over the veins, are found to be about 32° C. and above for most individuals at examining room temperatures of about 21°–25° C. Alternate sites for venipuncture, frequently used in intravenous therapy, include additional regions of the upper extremities, in particular, the hands, wrists, and remaining forearm regions, where the skin temperatures over veins selected for venipuncture generally are 30° C. or higher, and the lower extremities, i.e., the feet and legs, where the skin temperatures over the veins selected for venipuncture generally are 28° C. or higher. Accordingly, and in view of the optimum results obtained, it has been found preferable for widespread application to use liquid crystal compositions having mesophase temperature ranges as follows: up to about 33° C. for the antecubital fossa region, up to about 32° C. for both the antecubital fossa region and the upper forearm region, up to about 30° C. for all regions of the upper extremities, and up to about 28° C. for all regions of both the upper and lower extremities. Specific preferred mesophase temperature ranges lie between the following temperatures, approximately: 29° C. and 33° C. for the antecubital fossa region; 25° C. and 30° C. for all regions of the upper extremities, especially the hands, wrists, and forearms; and 23° C. and 28° C. for all regions of both the upper and lower extremities, especially the feet and legs. A further condition which has lead to optimum results is the selection of a mesophase temperature range of about 3°.

The selection of a mesophase temperature range lying within the range of 23° C.–30° C. is especially useful in intravenous therapy, where the more difficult cases are encountered. Thus, for example, sluggish blood flow is found in small, collapsed or plugged veins, resulting in lower skin temperatures and/or excessive delay in rewarming after cooling the skin. The provision of a mesophase temperature range in the range of 23° C.–30° C. markedly increases the number of patients that can be treated employing the venipuncture method, being especially suited for low skin temperatures while also being suited for higher skin temperatures, and providing a rapid vein indication.

The liquid crystal layer may be applied to the skin in the form of a paste, as a dispersion of the liquid crystals in a plastic film, or in the form of a layer of encapsulated liquid crystals. When applied in the form of a paste, the liquid crystals are admixed with a light-absorptive material to provide color contrast, the absorptive materials including dyes and pigments providing a dark background. Liquid crystal plastic resin dispersions and encapsulations preferably are coated over a darkened substrate providing the desired color contrast.

A preferred liquid crystal composition is disclosed in our above-identified U.S. Pat. No. 4,015,591. The composition disclosed therein comprises an enantiotropic cholesteric liquid crystalline phase material, such as described above, and at least two oil-soluble dyes dissolved in the material in a total dye concentration of 0.01–1% by weight of the composition, each of the dyes reflecting light of a different wave length in the range of 400 to 700 nanometers, and the dyes together absorbing light of substantially all wave lengths within such range. Preferably, the dyes together exhibit a violet, brown, or brown-black color at room temperature. Table 3 is a list of preferred dye combinations or mixtures for addition to the liquid crystals, composition numbers 1 and 2 being further preferred. Other dyes which may be employed are set forth in Table 3 of the aforesaid patent.

Table 3

| Dye Mixtures, in % by wt. of Composition | Color Combination at Room Temperature |
|---|---|
| 1. 0.1% C.I. Solvent Violet 13<br>0.02%–0.05% C.I. Solvent Yellow 33<br>0.02%–0.05% C.I. Solvent Red | Deep Violet |
| 2. 0.05% C.I. Solvent Violet 13<br>0.05% C.I. Solvent Yellow 33<br>0.05% C.I. Solvent Red 49 | Brown |
| 3. 0.1% C.I. Solvent Violet 17<br>0.1% C.I. Solvent Green 7 | Brown |
| 4. 0.1% C.I. Solvent Violet 13<br>0.1% C.I. Solvent Red 49<br>0.1% C.I. Solvent Yellow 5 | Brown-Black |
| 5. 0.2% C.I. Solvent Violet 13<br>0.1% C.I. Solvent Orange 2 | Violet |
| 6. 0.1% C.I. Solvent Violet 17<br>0.05% C.I. Solvent Yellow 5<br>0.05% C.I. Solvent Green 3 | Brown |

The paste composition of liquid crystals and dyes preferably is employed in a layer having a thickness of about 100 to 300 microns, thereby providing high color intensity as well as improved color contrast, as described in the patent. Inasmuch as organic solvents for the liquid crystals alter the optical effects, and in view of the difficulty in removing all traces of solvent, particularly in layer thicknesses of the foregoing magnitude, it is preferred that the composition be provided in the form of an organic solvent-free paste. Such a paste may be packaged in and dispensed from a tube, or from a pressurized container or other container adapted to dispense metered amounts or slugs of the paste, for example. The paste may be dispensed from a container under the pressure of a highly volatile solvent, such as one of the Freons, for example, which will evaporate very rapidly and not affect the optical properties of the liquid crystals. The paste may be spread on the skin in the desired thickness, using a tongue depressor, a spatula, a finger of the hand, or in another suitable manner.

Dispersions of liquid crystals in plastic resin films and suitable for use in the invention are disclosed in U.S. Pat. No. 3,620,889. A preferred film-forming polymer for use in making the film is polyvinyl butyral. It is preferred to provide color contrast by coating the dispersion on a dark plastic film substrate, employing conventional procedures.

Encapsulated liquid crystals which may be employed in the invention are disclosed in U.S. Pat. No. 3,585,381. The liquid crystals are microencapsulated in one of the materials and according to the procedures disclosed in the patent, such materials including gelatin-gum arabic, polyvinyl alcohol, zein, and others. It is preferred to bind the capsules with a transparent film-forming polymeric material, such as polyvinyl alcohol, as set forth in the patent, and deposit the capsules and binder on a darkened film substrate. The film material formed with liquid crystals dispersed in a film, or encapsulated and bound with a film-former, preferably is provided with an adhesive backing and cut into strips of tape for application to the skin.

Proceeding according to the invention, the skin over the venous area is cooled prior to venipuncture or venisection. In general, the cooling may take place before or after application of the liquid crystal layer. The purpose of the cooling is to produce a greater temperature gradient between the skin surface directly over a vein and adjacent areas of the skin, to thereby provide a sharper delineation of the vein. Cooling removes the heat supplied to the skin by various physiological sources, and thereafter, rewarming takes place most rapidly over the veins, due to the blood flow therein. We have found that where the temperature of the skin over the venous area initially is above the lower limit of the mesophase temperature range of the liquid crystals, substantially completely successful vein location, notably where deep veins are encountered, is achieved when the skin is cooled to bring it to a temperature at least 3° below the initial skin temperature and, preferably, to the temperature achieved by cooling with a cold pack, as described hereinafter, at a time immediately prior to rewarming by venous blood flow to produce the desired mesophase color change. Cooling to such extent insures that heat is removed from the areas adjacent to the vein sufficiently to produce a sharp vein pattern, without diffuse coloration resulting from the presence of other heat sources that otherwise could, at the same time, rewarm the skin adjacent to the vein into the mesophase temperature range.

While cooling had taken place in conjunction with application of liquid crystals to the skin in prior procedures, as described in the above-identified publications of Davison et al., there was no attempt to reach the foregoing degree of cooling, so far as is known, in view of the differences in the objectives of the published studies. U.S. Pat. No. 3,998,210 discloses the use of a cleansing agent which also cools the skin, but no such degree of cooling is disclosed.

The skin is cooled with a cold pack not only sufficiently, but also rapidly, uniformly and in a practical manner. Reference to a "cold pack" herein refers to a container filled with a mass having a minimum thermal capacity (the product of mass and specific heat) of 25 calories per degree centigrade and which is at a temperature between $-10°$ C. and $+10°$ C. Useful materials which may be employed in a suitable container include ice and icewater, frozen ethylene glycol, and frozen polyethylene glycol. These materials may be contained in a plastic bag or in a rigid metal container, for example. The cold pack is applied to the skin for at least about 3 seconds, and preferably for about 3 to 5 seconds. The skin temperature may be checked with a thermistor.

Cooling the skin for 3 seconds in the manner described hereinafter in Example 1 with the following cooling materials in plastic bags results in lowering the temperature of the skin over a vein, as measured with a thermistor, the amounts indicated for the respective materials: about 6.5°–8° C. lowering with water at 10° C.; about 9°–10° C. lowering with icewater at 0° C.; about 11°–13° C. lowering with ice at minus 10° C. The extent of cooling which may be effected with the cold pack thus is such that a liquid crystal composition may be employed which has a mesophase temperature range substantially lower than the skin temperature over a venous area, permitting a single composition to be used successfully both for the higher and the lower skin temperatures encountered. This advantage is illustrated hereinafter in Example 7.

It is preferable to cool the skin over the venous area to bring it to a temperature below the lower limit of the mesophase temperature range of the liquid crystals. When this condition is observed, a very fine delineation of the vein appears as the initial or first mesophase color change, contrasted against the background. Consequently, the best site for needle insertion into a vein is accurately located, and also, the best vein for needle insertion may be determined.

The liquid crystal layer is applied directly on the skin over the venous area, so that it extends transversely across the veins, in a strip approximately 1 centimeter wide. In using the paste, a slug of the paste is dispensed onto a tongue depressor, for example, and the paste is spread with the tongue depressor held at an acute angle to the skin. With a film strip, the strip is merely adhered to the skin. Most frequently, the liquid crystal layer extends transversely across the arm in the antecubital fossa area. With the use of a film strip, the above-described cooling may be effected as well after applying the film strip to the skin as before. It is less convenient to after-cool the skin following application of the paste.

Following the cooling and application of liquid crystals, an indication of a vein generally appears in from about several seconds up to about 30 seconds, depending upon the rapidity of operation and physiological factors. The venous area is the most rapidly rewarming area, and is indicated by the first color to appear, following cooling to below the mesophase temperature range, and thereafter, by the shortest wave length color present. As the skin continues to warm, the color of the venous area goes through the above-described color changes from red to violet, to the extent that the skin reaches a temperature corresponding to a particular color of the liquid crystals. The specific appearance of the venous area will vary under varying circumstances, and it may appear as a line, an elliptical area, or a spot.

The above-described first appearance of color precisely indicates the location of the best site for insertion of a needle in each vein that appears. As a general rule, it is preferable to mark the skin at the location of the first appearance of color, by a blunt instrument, such as a cylindrical rod of small diameter or the like, pressed against the skin. As the skin continues to warm, the color change extends along the vein, and also diffuses outwardly. It is then preferable that a second mark be made in the colored area over the vein, which is distal to the first mark, to indicate the direction of the vein. These marks or impressions properly made will remain in the skin for ample time to permit subsequent venipuncture. The marking procedure applies particularly to use of the liquid crystal paste, which in the preferred procedure is removed following vein location, although marks may be made on the skin by pressing against thin films thereon. Alternatively, with the use of films, and also with the paste, the skin area distal to the liquid crystal layer may be marked, or venipuncture may be made in such area without marking and while guided by the color change which is taking place or has taken place in the liquid crystal layer.

The best delineation of vein sites and patterns is observed when colors first appear: delineation of vein locations becomes diffuse as warming continues, due to lateral heat diffusion. Diffuse and imprecise vein locations also result when the skin is not cooled adequately, inasmuch as the colors appear and diffuse too quickly. The rate of color development, corresponding to skin temperature elevation, over a vein after cooling is directly proportional to blood temperature, blood flow, and vein size, and inversely proportional to vein depth beneath the skin. The information thus obtained enables phlebotomists and I.V. therapists to determine the most desirable vein for venipuncture and the most desirable location on the vein for venipuncture, as well as the direction of the vein for needle or catheter insertion.

Preferably, a tourniquet is applied following the foregoing procedural steps, inasmuch as optimum results are obtained with normal venous blood flow. Following the observation of mesophase color change and marking of the skin, the liquid crystal paste where used is removed by wiping well with rubbing alcohol or other alcohol antiseptic, to remove the liquid crystals and sterilize the area, including the area in which the needle is to be inserted. The marks made as described above are employed by the technician as indicators of the best site and direction for needle insertion. In a preferred procedure, the needle is inserted at the second mark and directed toward the first mark, at an acute angle to the vein. Alternatively, and especially with more experienced technicians, the liquid crystal layer, whether paste or film, may remain on the skin, while an area adjacent thereto is sterilized for venipuncture, at a distance of about ½ centimeter distal to the liquid crystal layer. The entire procedure is completed in a relatively short period of time by a competent technician.

Where rewarming to bring the skin temperature over a vein to the mesophase temperature range is relatively slow, increases in the blood temperature and flow rate may be induced. Induction procedures include preferably warming the fingers or toes to about 35° C.–45° C., by immersion in water or wrapping with a warm towel or heating device, and exercising forearm or leg muscles.

The following examples illustrate the manner in which venipuncture may be effected in accordance with the invention. It will be understood that the invention is not limited to the materials, proportions, conditions and procedures employed in the examples, which are merely illustrative.

EXAMPLE 1

In the preparation of liquid crystal compositions or materials in organic solvent-free paste form, 100-gram quantities of the compositions numbered 1(31°–34° C.), 8(29°–33° C.), and 18(29°–32° C.) in Table 2 in formulated in Pyrex beakers and heated to melting temperature on a hot plate with gentle stirring, employing a magnetic stirring bar. The mixtures become single phase liquids upon heating for one minute at 60° C.

A mixture of dyes is dissolved in each molten liquid crystal mixture at 60° C., the dye mixture containing the following dyes in the proportions indicated:

| Component | Proportion, Grams |
| --- | --- |
| C.I. Solvent Violet 13 | 0.10 |
| C.I. Solvent Yellow 33 | 0.05 |
| C.I. Solvent Red 23 | 0.05 |

The resulting compositions may be packaged in five 1-ounce ointment tubes, in 20-gram aliquots. The tubes are cooled at room temperature to 25°–30° C., and the tubes are crimped to seal them. Each tube contains a composition in paste form and can be used for 40–60 vein locations.

In one manner of effecting venipuncture, which is generally applicable to the majority of individuals, having skin temperatures of about 33° C. and higher, a skin area for vein location is selected in the forearm, adjacent to the elbow. The area is cooled with icewater in a plastic bag applied on the skin and rubbed uniformly over the area for 3 to 5 seconds, thereby reducing the skin temperature by at least 3° C. and below the mesophase temperature range of the composition to be applied. About 0.3 to 0.5 gram of one of the compositions is applied to the tip of a tongue depressor, and the composition is spread transversely across the arm in a strip about 1 cm. wide with the depressor held at an acute angle. The composition assumes the color of the dye mixture. The first mesophase color usually appears within several seconds. The warmest temperatures, corresponding to vein locations, are indicated by the first appearance of red color and, thereafter, by the color of the shortest wave length, which most frequently appears as elliptical lines over superficial veins.

A vein location identified by a colored area may be marked by a slight depression in the skin, made with a 1/16 inch diameter rod. A mark is made where the mesophase color first appears, to show the best position to puncture the vein. A second mark distal to the first mark is made in the colored area as it extends, to show the direction of the vein. The liquid crystal composition then may be removed from the skin and the skin sterilized by wiping with cotton soaked in aqueous isopropanol or ethanol-diethyl ether. A tourniquet is applied to the arm. A needle is directed to a site in the arm beneath the first mark in the skin, being inserted in the skin at the second mark and directed through the subcutaneous tissues at an angle to the skin towards the first mark, for puncturing the vein with the needle at an acute angle thereto. Alternatively, the needle may be inserted while the composition remains to indicate the vein location, in which case, the insertion is made at a location distal to the skin area covered with the liquid crystal composition, after first sterilizing the insertion site.

EXAMPLE 2

A 100-gram quantity of liquid crystal composition number 2(30°–37° C.) of Table 2 is compounded with dye mixture number 2 of Table 3, following the procedure of Example 1. The resulting paste composition may be employed in effecting venipuncture, in the same general manner as with the compositions of Example 1.

EXAMPLE 3

A 100-gram quantity of liquid crystal composition number 9(28°–33° C.) of Table 2 is formulated following the procedure of Example 1. A carbon black powder is added to the composition during vigorous agitation, in a proportion in the range of 0.1% to 5% by weight of the total composition. The resulting paste composition may be employed in effecting venipuncture in the same manner as with the compositions of Example 1.

EXAMPLE 4

A 10-gram quantity of liquid crystal composition number 17(30°–33° C.) of Table 2 is dispersed in 100 grams of a 15% by weight solution of polyvinyl butyral in isopropyl alcohol. The polyvinyl butyral has a molecular weight range of 180,000–270,000, a hydroxy content in the range of 17.5–20%, and an acetate content in the range of 0–2.5%.

The dispersion is knife-coated or sprayed in a layer about 5–10 mils thick when wet on a black Mylar (2 mils thick) (polyethylene glycol terephthalate) substrate. The coating is air-dried to eliminate the isopropyl alcohol, leaving a dry layer about 0.4–0.6 mil in thickness containing the liquid crystals dispersed in a polyvinyl butyral film. A pressure-sensitive adhesive backing of water-dispersible polyvinyl acetate in aqueous dispersion (Bordon Chemical) is provided on the substrate. The film supported on the substrate is cut into 1 cm. by 8 cm. strips of tape. The tape has a 30°–33° C. mesophase temperature range.

Veins can be located and venipuncture effected in the antecubital fossa of individuals having skin temperatures thereat of about 33° C. and higher, as follows: preferably following an antiseptic wipe, a liquid crystal tape is applied to the skin transversely across the antecubital fossa, with the pressure-sensitive adhesive backing adhering thereto. The tape and underlying skin are cooled to below 30° C. and at least 3° C. below the initial skin temperature by applying an ice bag on the tape and surrounding skin areas for 3 to 5 seconds, at which time, the tape appears black. Thereafter, mesophase color appears over the vein sites within several seconds.

The skin area immediately distal to the tape is prepared for needle insertion with an antiseptic wipe, when color first appears. A tourniquet is applied, and a needle is inserted at a location spaced below the tape and at an acute angle such that the located vein is punctured beneath the area of the tape where color first appeared, indicating the best site for venipuncture. The tape may be stripped from the skin at any time after the vein is located.

EXAMPLE 5

Liquid crystal composition number 18(29°–32° C.) of Table 2 is dispersed in a plastic film and incorporated in a tape having a 29° C.–32° C. temperature range in the manner described in Example 4. Veins can be located in the hands of patients with poor circulation as follows: a tape is applied to the skin transversely across the dorsum of the hand. The tape and the underlying skin is cooled to a temperature at least 3 degrees below the warmest skin temperature and below 29° C. by applying to the skin a cold pack, such as an ice pack, for a period of about 3 to 5 seconds. When the warmest temperature of the hand is above 29° C. but not 32° C. or above, it may be desirable to immerse the fingers of the hand in warm (40°–45° C.) water following the cooling, in order to increase circulation and accelerate the color response.

A mesophase color appears on the liquid crystal tape over a vein, showing its location. The skin area immediately adjacent to the tape then is prepared for needle insertion by an antiseptic wipe. A tourniquet is applied, and a needle is inserted at a site spaced from the tape, to puncture the vein, in the manner described in Example 4.

In a further alternative, a liquid crystal composition having a lower mesophase temperature range may be substituted in the film or compounded in a paste composition as in Example 1, and used for venipuncture following the general procedure of Example 1.

EXAMPLE 6

Liquid crystal composition number 11(31°–33° C.) of Table 2 is microencapsulated in gelatin-gum arabic capsules according to the procedure of U.S. Pat. No. 3,585,381. The capsules are dispersed in an equal volume of a 10% by weight solution of polyvinyl alcohol in water. The dispersion is coated in a thin layer on a black Mylar substrate of 2 mil thickness, and the substrate is provided with a water-dispersible acetate pressure-sensitive adhesive backing. The product may be cut into strips of tape and employed similarly to the tape of Example 4.

EXAMPLE 7

Liquid crystal composition number 17(30°–33° C.) of Table 2 was mixed with the dye mixture and in the proportions described in Example 1. The composition was employed in a hospital for vein location and evaluation, in the course of intravenous therapy. The subjects were randomly selected difficult cases, having obscure, deep, and/or small veins, or other complications.

The venipuncture procedure of Example 1 was followed, in general, for locating veins in the hand, wrist, lower forearm, or, rarely, in the upper arm. Icewater (0° C.) in plastic bags was employed for cooling the skin over a venous area for a period of about 3–5 seconds. After removing the liquid crystal composition with an alcohol wipe and prior to the application of a tourniquet and insertion of a catheter, the injection site was prepared in the usual manner by sterilization with Betadine.

Veins in which catheters were successfully inserted were located in 38 of 54 patients (70%) on which the venipuncture procedure was used. In the absence of such procedure, rigorous and often excessively painful procedures are required.

Subsequently, in an effort to achieve an even higher rate of success, the new venipuncture method was followed, employing composition number 22(27°-30° C.) of Table 2, mixed with the same dye mixture and in the same proportions as described in Example 1. The procedure otherwise was the same as described above for the use of composition number 17.

Veins in which catheters were successfully inserted were located in 12 of 14 patients (86%) on which composition number 22 was used. The improvement was attributed to the lower mesophase temperature range of the latter composition, which was suited for locating veins where skin temperatures were lower than median temperatures, and also was suited for locating veins where skin temperatures were in the median range, the latter by virtue of the substantial cooling produced by application of the icewater cold pack, readily bringing the skin temperature below the mesophase temperature range, as with the lower initial skin temperatures.

While certain preferred embodiments of the invention have been described, it will be apparent to those skilled in the art that various changes and modifications may be made therein within the spirit and scope of the invention. It is intended that such changes and modifications be included within the scope of the appended claims.

We claim:

1. A method of effecting venipuncture in the human body which comprises the steps of:
   (a) cooling the skin over a venous area of the body by applying a cold pack thereto for a period of at least 3 seconds and providing on the cooled skin in heat exchange relation thereto a layer of an enantiotropic cholesteric liquid crystalline phase material exhibiting a mesophase color change at a temperature reached by the skin upon warming by venous blood flow, the lower limit of the mesophase temperature range of said material being below the initial temperature of the skin over said area, said cooling being effected to bring the skin over said area to a temperature below said lower limit;
   (b) warming the cooled skin by venous blood flow in said area thereby to produce a mesophase color change in the material in said layer delineating a vein beneath the layer; and
   (c) directing an instrument for venipuncture to a site in said area indicated by said delineation to constitute the location of a vein.

2. A method as defined in claim 1 and wherein said site is the site over which appears the initial mesophase color change indicating a vein selected for venipuncture.

3. A method as defined in claim 1 and wherein said mesophase temperature range lies between about 29° C. and 33° C.

4. A method as defined in claim 1 and wherein said mesophase temperature range lies between about 20° C. and 40° C.

5. A method as defined in claim 1 and wherein said layer comprises an organic solvent-free paste of said material.

6. A method as defined in claim 1 and wherein said layer comprises a dispersion of said material in a plastic film.

7. A method as defined in claim 6 and wherein said plastic is polyvinyl butyral.

8. A method as defined in claim 1 and wherein said material is encapsulated.

9. A method as defined in claim 1 and wherein said cold pack includes a coolant at a temperature in the range of about 0° C. to −10° C., and said mesophase temperature range lies between about 20° C. and 40° C.

10. A method as defined in claim 9 and wherein said coolant is ice.

11. A method as defined in claim 9 and wherein said coolant is icewater.

12. A method as defined in claim 9 and wherein said layer comprises a dispersion of said material in a polyvinyl butyral film.

13. A method of effecting venipunctue in the human body which comprises the steps of:
   (a) cooling the skin over a venous area of the body by applying a cold pack thereto for a period of at least 3 seconds and providing on the cooled skin in heat exchange relation thereto a layer of an enantiotropic cholesteric liquid crystalline phase material having a mesophase temperature range width of about 1° C. to 7° C., the upper limit of said range being at most about equal to and the lower limit of said range being below the initial temperature of the skin over said area, said cooling being effected to bring the skin over said area to a temperature below said lower limit;
   (b) warming the cooled skin by venous blood flow in said area thereby to produce a mesophase color change in the material in said layer delineating a vein beneath the layer; and
   (c) directing an instrument for venipuncture to a site in said area indicated by said delineation to constitute the location of a vein.

14. A method as defined in claim 13 and wherein said site is the site over which appears the initial mesophase color change indicating a vein selected for venipuncture.

15. A method s defined in claim 13 and wherein said mesophase temperature range lies between about 29° C. and 33° C.

16. A method as defined in claim 13 and wherein said mesophase temperature range lies between about 20° C. and 40° C.

17. A method as defined in claim 13 and wherein said cold pack includes a coolant at a temperature in the range of about 0° C. to −10° C., and said mesophase temperature range lies between about 20° C. and 40° C.

18. A method as defined in claim 17 and wherein said coolant is ice.

19. A method as defined in claim 17 and wherein said coolant is icewater.

20. A method as defined in claim 17 and wherein said layer comprises a dispersion of said material in a polyvinyl butyral film.

* * * * *

UNITED STATES PATENT AND TRADEMARK OFFICE
CERTIFICATE OF CORRECTION

PATENT NO. : 4,175,543
DATED : November 27, 1979
INVENTOR(S) : Fred K. Suzuki and Thomas W. Davison It is certified that error appears in the above-identified patent and that said Letters Patent are hereby corrected as shown below:

Column 1, line 42, after "edema," insert --phlebitis,--;

Column 3, line 19, after "material" insert --exhibiting--.

Column 4, line 36, in Table 1 after "Cholesteryl hexanoate (CHx)" insert --Cholesteryl laurate (CLa)--.

Column 10, line 15, change "in" second occurrence to --are--.

Signed and Sealed this

Twenty-fifth Day of March 1980

[SEAL]

Attest:

SIDNEY A. DIAMOND

Attesting Officer

Commissioner of Patents and Trademarks